US009452960B2

(12) United States Patent  
Guerra et al.

(10) Patent No.: US 9,452,960 B2
(45) Date of Patent: Sep. 27, 2016

(54) PARTIALLY FLUORINATED COMPOUNDS

(71) Applicant: 3M INNOVATIVE PROPERTIES COMPANY, St. Paul, MN (US)

(72) Inventors: Miguel A. Guerra, Woodbury, MN (US); Tatsuo Fukushi, Woodbury, MN (US); Kenneth D. Wilson, Marine on the St. Croix, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 14/649,666

(22) PCT Filed: Nov. 27, 2013

(86) PCT No.: PCT/US2013/072149
§ 371 (c)(1),
(2) Date: Jun. 4, 2015

(87) PCT Pub. No.: WO2014/093024
PCT Pub. Date: Jun. 19, 2014

(65) Prior Publication Data
US 2016/0185693 A1  Jun. 30, 2016

Related U.S. Application Data

(60) Provisional application No. 61/737,275, filed on Dec. 14, 2012.

(51) Int. Cl.
C08F 12/20 (2006.01)
C08F 18/20 (2006.01)
C07C 19/16 (2006.01)
C07C 17/093 (2006.01)
C07C 17/20 (2006.01)
C07C 17/25 (2006.01)
C07C 17/278 (2006.01)
C08F 214/18 (2006.01)
C08K 3/04 (2006.01)
C08K 5/14 (2006.01)
C08K 5/3492 (2006.01)
C07C 21/18 (2006.01)
C08F 236/18 (2006.01)

(52) U.S. Cl.
CPC ............ *C07C 19/16* (2013.01); *C07C 17/093* (2013.01); *C07C 17/204* (2013.01); *C07C 17/25* (2013.01); *C07C 17/278* (2013.01); *C07C 21/18* (2013.01); *C08F 214/18* (2013.01); *C08F 236/18* (2013.01); *C08K 3/04* (2013.01); *C08K 5/14* (2013.01); *C08K 5/34924* (2013.01)

(58) Field of Classification Search
CPC ... C07C 17/093; C07C 17/204; C07C 17/25; C07C 17/278; C07C 19/16; C07C 21/19; C07C 21/18; C08F 214/18; C08K 3/04; C08K 5/14; C08K 5/34924; C08L 27/12

USPC .................................................. 526/242, 245
See application file for complete search history.

(56) References Cited

U.S. PATENT DOCUMENTS

| 2,732,398 A | 1/1956 | Brice |
| 2,975,220 A | 3/1961 | Hauptschein |
| 3,106,589 A | 10/1963 | Hauptschein |
| 4,243,779 A | 1/1981 | McAlister |
| 4,361,678 A | 11/1982 | Tatemoto |
| 4,587,366 A | 5/1986 | Von Werner |
| 6,150,565 A | 11/2000 | Yang |
| 6,429,258 B1 | 8/2002 | Morgan |
| 6,610,790 B2 | 8/2003 | Hung |
| 7,951,983 B2 | 5/2011 | Peng |
| 2002/0002248 A1 | 1/2002 | Hung |
| 2007/0015937 A1 | 1/2007 | Hintzer |

FOREIGN PATENT DOCUMENTS

| JP | 1-180837 | * 7/1989 |
| WO | WO 2007-074632 | 7/2007 |
| WO | WO 2007-091517 | 8/2007 |
| WO | WO 2014-062450 | 4/2014 |
| WO | WO 2014-062469 | 4/2014 |

OTHER PUBLICATIONS

Manseri, "Synthesis of Fluorinated telomers Part 4. Telomerization of vinylidene fluoride with commercially available dliodoperfluoroalkanes", Journal of Fluorine Chemistry, 1995, vol. 74, pp. 59-67.*
Manseri, "Unexpected telomerization of hexafluoropropene with dissymmetrical halogenated telechelic telogens", Journal of Fluorine Chemistry, 1996, vol. 78, pp. 145-150.*
Manseri, "Synthese de dienes telecheliques a partir d' a,m-diiodo-alcanes fluores Partie II: Divinyls et diallyls presentant des motifs constitutifs tetrafluoroethylene, fluorure de vinylidne et hexafluoropropene", Journal of Fluorine Chemistry, 1997, vol. 81. pp. 103-113.
Manseri, "Synthesis of Fluorinated telomers Part 4. Telomerization of vinylidene fluoride with commercially available diiodoperfluoroalkanes", Journal of Fluorine Chemistry, 1995, vol. 74, pp. 59-67.
Rondestvedt, Jr., "Methyl-terminated perfluoroalkyl iodides and related compounds", The Journal of Organic Chemistry, May 1977, vol. 42, No. 11, pp. 1985-1990.
International Search Report for PCT Application No. PCT/US2013/072149 mailed on Mar. 24, 2014, 5 pages.

* cited by examiner

*Primary Examiner* — William Cheung
(74) *Attorney, Agent, or Firm* — Julie Lapos-Kuchar

(57) ABSTRACT

Described herein is a composition comprising a partially fluorinated compound selected from the group consisting of: (a) $I(CF_2)_xCH_2CF_2I$; (b) $ICF_2CH_2(CF_2)_xCH_2CF_2I$; (c) $I(CF_2)_yCH=CF_2$; (d) $CF_2=CH(CF_2)_yCH_2CF_2I$; and (e) $CF_2=CH(CF_2)_yCH=CF_2$ wherein x is an odd integer selected from 3 to 11, and y is an integer greater than 2, along with methods of making and polymerizing such compounds.

15 Claims, No Drawings

PARTIALLY FLUORINATED COMPOUNDS

CROSS REFERENCE TO RELATED APPLICATIONS

This application is a national stage filing under 35 U.S.C. 371 of PCT/US2013/072149, filed Nov. 27, 2013, which claims priority to U.S. Provisional Application No. 61/737,275, filed Dec. 14, 2012, the disclosure of which is incorporated by reference in their entirety herein.

TECHNICAL FIELD

Partially fluorinated compounds are described, along with methods of making thereof. These partially fluorinated compounds may be used in the preparation of fluoropolymers.

SUMMARY

There is a desire to find alternative partially fluorinated compounds for use in polymer synthesis.

In one embodiment, there is also a desire to provide partially fluorinated compounds for polymer synthesis that react more quickly and/or provide higher incorporation into the polymer. It would also be desirable to identify methods of making fluoroiodo compounds that may be more efficient and/or cheaper than traditional methods.

In one aspect, a composition is provided comprising a partially fluorinated compound selected from the group consisting of:
(a) $I(CF_2)_x(CH_2CF_2I)$;
(b) $ICF_2CH_2(CF_2)_xCH_2CF_2I$;
(c) $I(CF_2)_yCH=CF_2$;
(d) $CF_2=CH(CF_2)_yCH_2CF_2I$; and
(e) $CF_2=CH(CF_2)_yCH=CF_2$
wherein x is an odd integer selected from 3 to 11, and y is an integer greater than 2.

In another aspect, a polymer composition is provided comprising the polymerized reaction product of the following reactants: (a) a first compound selected from the partially fluorinated compound of: $I(CF_2)_xCH_2CF_2I$; $ICF_2CH_2(CF_2)_xCH_2CF_2I$; $I(CF_2)_yCH=CF_2$; $CF_2=CH(CF_2)_yCH_2CF_2I$; and $CF_2=CH(CF_2)_yCH=CF_2$, wherein x is an odd integer selected from 3 to 11, and y is an integer greater than 2; and (b) a second compound comprising a fluorinated olefinic monomer.

In one aspect, a method of making a polymer is provided comprising: (a) providing a first fluorinated olefinic monomer comprising the partially fluorinated compound, $I(CF_2)_yCH=CF_2$ wherein y is an integer greater than 2; a second fluorinated olefinic monomer; and an initiator; and (b) polymerizing the first and second fluorinated olefinic monomers in the presence of the initiator to form a polymer.

In another aspect, a method of making a polymer is provided comprising: (a) providing a first fluorinated olefinic monomer comprising the partially fluorinated compound, $CF_2=CH(CF_2)_yCH=CF_2$ wherein y is an integer greater than 2; a second fluorinated olefinic monomer; and an initiator; and (b) polymerizing the first and second fluorinated olefinic monomers in the presence of the initiator to form a polymer.

In yet another aspect, a method of making a partially fluorinated compound is provided comprising reacting a molecule of the formula $I(CF_2)_xI$ with 1,1-difluoroethylene to form $I(CF_2)_xCH_2CF_2I$, wherein x is an odd integer selected from 3 to 11.

In yet another aspect, a method of making a partially fluorinated compound is provided comprising reacting a molecule of the formula $I(CF_2)_xI$ with 1,1-difluoroethylene to form $ICF_2-CH_2(CF_2)_yCH_2CF_2I$, wherein y is an integer greater than 2.

In yet another aspect, a polymer obtainable by polymerizing (a) a first compound selected from the partially fluorinated compound of: $I(CF_2)_xCH_2CF_2I$ (Formula I); $ICF_2CH_2(CF_2)_xCH_2CF_2I$ (Formula II); $I(CF_2)_yCH=CF_2$ (Formula III); $CF_2=CH(CF_2)_yCH_2CF_2I$ (Formula IV); and $CF_2=CH(CF_2)_yCH=CF_2$ (Formula V) wherein x is an odd integer selected from 3 to 11, and y is an integer greater than 2; and (b) a second compound comprising a fluorinated olefinic monomer is provided.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more; and
"and/or" is used to indicate one or both stated cases may occur, for example A and/or B includes, (A and B) and (A or B).

The term "polymer" refers to macromolecules made up of interpolymerized monomer units. Polymers comprise large numbers (e.g., hundreds or more) interpolymerized monomer units and have high molecular weights e.g., over 10,000 grams/mole.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 3, at least 4, at least 6, at least 8, at least 10, at least 25, at least 50, at least 100, etc.).

α,ω-Diiodoperfluoroalkanes are important building blocks in the preparation of other fluorinated compounds and polymers. In fluoropolymers, the α,ω-diiodoperfluoroalkanes are used as chain transfer agents, helping to control the molecular weight of the polymer. Typically, these α,ω-diiodoperfluoroalkanes are made from telomerization of tetrafluoroethylene with iodine resulting in even numbered $CF_2$ units. See, for example J. Org. Chem., v.42, no. 11, p. 1985-1990 (1977). Further, iodo-compounds can be polymerized into the polymer and the presence of iodide in fluoropolymer is useful for crosslinking.

Fluorinated diiodides with an odd number of $CF_2$ units have been difficult and costly prepare. Fluorinated diiodides with an odd number of $CF_2$ units have been made by reacting $ICF_2I$ with tetrafluoroethylene, however, tetrafluoroethylene can be hard to handle and $ICF_2I$ is not readily available. Recently, Applicants have discovered a preparation for perfluorinated diiodides having an odd number of $CF_2$ units. As disclosed in U.S. Appl. No. 61/715,413 (filed Oct. 18, 2012), ethylene is inserted into a perfluorinated diiodo-compound to form, among other things, odd numbered partially fluorinated diiodo compounds, which can be used in polymer synthesis.

Using a similar reaction scheme as disclosed in U.S. Appl. No. 61/715,413 (filed Oct. 18, 2012), Applicants have discovered that insertion of vinylidene fluoride into a perfluorinated diiodo-compound can lead to partially fluorinated compounds having improved performance in polymer synthesis.

Previously, vinylidene fluoride has been reacted with fluorocarbon monoiodides to give low molecular weight polymers as described in U.S. Pat. No. 2,975,220, which can be used as lubricants and hydraulic fluids. U.S. Pat. No. 6,150,565 described reactions of $CF_2I_2$ with olefins including vinylidene fluoride. U.S. Pat. No. 6,610,790 described the reaction of and perfluoroiodo alkane with vinylidene fluoride, which is then further reacted to form a partially fluorinated alkene (e.g., $C_4F_9CH_2CF_2CH=CF_2$).

In the present disclosure, it has been discovered that insertion of VDF into perfluorinated diiodo compounds can lead to new small molecules, which can be used in fluoropolymer synthesis. Such compounds may be used as chain transfer agents, cure site monomers, or even monomers during a polymerization. In one embodiment, it has been discovered that cure site monomers of the present disclosure may be more compatible with fluoroolefin comonomers, enabling fast reaction rates with higher incorporation as compared to their ethylene inserted counterpart.

The present disclosure is directed towards the preparation of partially fluorinated compounds, comprising iodine, a carbon-carbon double bond, or a combination thereof.

In the present disclosure, a process for making an vinylidene fluoride-substituted perfluorodiiodide compound is disclosed, wherein a perfluorinated diiodo-compound is reacted with vinylidene fluoride ($CH_2=CF_2$) to form partially fluorinated α,ω-diiodo compounds. The partially fluorinated α,ω-diiodo compounds can then be dehydroiodinated to form partially fluorinated iodoalkene compounds (i.e., compounds comprising a terminal iodine atom on one side of the molecule and a terminal carbon-carbon double bond on the opposing side of the molecule), and partially fluorinated dialkene compounds (i.e., compounds comprising a two terminal carbon-carbon double bond on opposing sides of the molecule).

Shown below are exemplary reactions of the present disclosure, wherein the perfluorinated diiodo-compound starting material is a perfluorinated α,ω-diiodoalkane of the formula $I(CF_2)_aI$ where a is an integer greater than 2 and no more than 20 (e.g., a is, 3, 4, 5, 6, 7, 8, 9, 10, 11, 12, 13, 14, 15, 16, 17, 18, 19, or 20). Note that although the following reaction schemes start with a perfluorinated α,ω-diiodoalkane and illustrate resulting linear alkane and linear alkene compounds, the chemistries described in Methods I-III may be applied similarly to when other perfluorinated diiodo-compounds are used.

Method I:

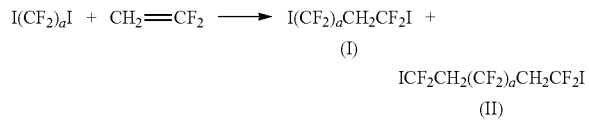

Method II:

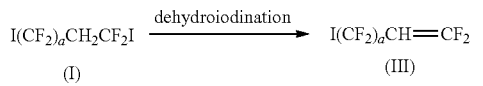

Method III:

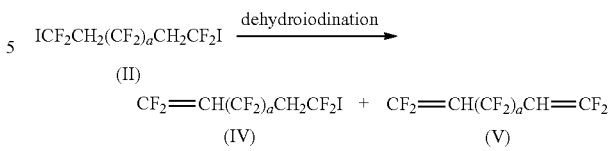

The above described reaction schemes will be discussed below in more detail.

Method I

In Method I, a perfluorinated diiodo-compound is reacted with vinylidene fluoride, VDF, to form a partially fluorinated alpha, omega-diiodo compound.

In one embodiment, the perfluorinated diiodo-compound is a α,ω-diiodoperfluorinated compound of formula $ICF_2R_fCF_2I$, wherein $R_f$ is a divalent, perfluorinated linking group. The α,ω-diiodoperfluorinated compound may be obtained commercially or made using techniques known in the art. In one embodiment, perfluorodisulfonyl fluoride can be reduced and then reacted with iodine to form a perfluorinated diiodo-compound as disclosed in for example, U.S. Appl. No. 61/715,413 (filed Oct. 18, 2012), herein incorporated by reference. In another embodiment, an α,ω-diiodoperfluoroalkane can be made by reacting hexafluoropropylene oxide with iodine as disclosed in, for example, U.S. Appl. No. 61/715,059 (filed Oct. 17, 2012), herein incorporated by reference. Alternatively, a α,ω-diiodoperfluoroalkane can be made by a process including known processes of making α,ω-diiodoperfluoroalkanes, such as TFE telomerization. However, the telomerizaion processes may not favor the formation of odd numbered carbon chain length, which may be desirable in some instances.

In one embodiment, the perfluorinated diiodo-compound comprises a cyclic moeity and/or branching and/or catenary heteroatoms. Typically the perfluorinated linking group ($R_f$) comprises at least 1, 2, 3, 4, 5, 7 or even 9 carbon atoms. In one embodiment, the perfluorinated linking group is linear. In another embodiment, the perfluorinated linking group can contain branching groups having 1 to 5 carbon atoms and, if sufficiently large, cyclic groups. In an alternative embodiment, the perfluorinated linking group comprises catenary heteroatoms such as nitrogen, sulfur, or oxygen.

Exemplary perfluorinated diiodo-compounds include α,ω-diiodoperfluoroalkane of formula $I(CF_2)_aI$, wherein a is an integer of at least 3 and at most 20 (i.e., a is 3, 4, 5, 6, 7, etc), such as $I(CF_2)_3I$, $I(CF_2)_4I$, $I(CF_2)_5I$, $I(CF_2)_6I$, $I(CF_2)_7I$, and $I(CF_2)_8I$.

In the reaction of Method I, vinylidene fluoride (VDF, $CF_2=CH_2$) is inserted into the perfluorinated diiodo-compound. To achieve the insertion of the VDF, either a radical forming compound, light (such as UV radiation), and/or heat is used.

Exemplary radical forming compounds include, peroxides or azo compounds. Peroxides include, for example, organic peroxides, such as diacyl peroxides, peroxyesters, dialkyl peroxides, and hyrdoperoxides. Azo compounds include, for example, azoisobutyronitrile and azo-2-cyanovaleric acid. Other radical forming compounds are electron donors, such as metal or metal complexes with ligands as well known in the literature. Exemplary electron donor for such addition of perfluorinated iodide with unsaturated carbon-carbon bond are Cu, Zn, Mg, Pd(0), Fe, Ni, Pt(P($C_6H_5$)$_3$)$_4$, Ir(CO)H(P($C_6H_5$)$_3$)$_3$, Pb($C_2H_3O_2$)$_4$ and RhCl(P($C_6H_5$)$_3$)$_2$.

In one embodiment the reaction may be conducted at a temperature of at least 10, 25, 50, 100, or even 125° C.; at most 140, 150, 200, or even 220° C.

In one embodiment, the reaction with the VDF is conducted neat. In another embodiment, the reaction with the VDF is conducted in the presence of a solvent. Typical solvents include inert solvents, for example, fluorinated solvents such as those available under the trade designation "3M FLUORINERT ELECTRONIC LIQUID" and "3M NOVEC ENGINEERED FLUID" from 3M Co., St. Paul, Minn.

In one embodiment, the ratio of the perfluorinated diiodo-compound to VDF is 1:2.5 to 2.5:1. As shown in the exemplary reaction of Method I above, when doing the insertion of VDF into the perfluorinated diiodo-compound, the 1:1 adduct (e.g., Formula I) or the 1:2 adduct (i.e., 1 equivalent of the perfluorinated diiodo-compound to 2 equivalents of VDF, e.g., Formula II) may be formed. The ratio of VDF to the perfluorinated diiodo-compound may be adjusted to favor a particular adduct. For example, to favor the formation of the 1:1 adduct, the ratio of the perfluorinated diiodo-compound to VDF is 1:0.8 to 1:1.1. To favor the formation of the 1:2 adduct, the ratio of the perfluorinated diiodo-compound to VDF is 1:1.8 to 1:2.5. Additionally, the reaction conditions (including temperature, reaction time, pressure, and/or stir speed) may be controlled and optimized to favor a particular adduct.

The resulting VDF substituted perfluorodiiodide (i.e., a partially fluorinated $\alpha,\omega$-diiodo compound) may be isolated and purified by known methods.

The number of carbons in the resulting partially fluorinated $\alpha,\omega$-diiodo compound is identical to the number of carbons present in the perfluorinated diiodo-compound starting material plus the two carbons from VDF. Therefore, Method I as disclosed above may be used to generate both odd numbered and even numbered partially fluorinated $\alpha,\omega$-diiodo compounds, depending on the carbon length of the initial starting material. For example, if a $\alpha,\omega$-diiodoperfluoroalkane comprises three $CF_2$ groups than the resulting partially fluorinated $\alpha,\omega$-diiodoalkanes will have four $CF_2$ groups and one $CH_2$ group. Likewise, if the $\alpha,\omega$-diiodoperfluoroalkane comprises four $CF_2$ groups than the resulting partially fluorinated $\alpha,\omega$-diiodoalkanes will have five $CF_2$ groups and one $CH_2$ group. Furthermore, if the perfluorinated diiodo-compound comprises a moiety of $-CF_2 CF(CF_3)CF_2-$ than the resulting partially fluorinated $\alpha,\omega$-diiodo compound will also comprise a moiety of $-CF_2 CF(CF_3)CF_2-$ plus a $CH_2CF_2$ group.

In one embodiment, partially fluorinated $\alpha,\omega$-diiodo compounds made by the process of Method I include those of: $I(CF_2)-CH_2CF_2I$; $ICF_2CH_2(CF_2)_xCH_2CF_2I$ where x is an odd integer selected from 3, 5, 7, 9, or 1; and combinations of these formulas.

In one embodiment, exemplary partially fluorinated $\alpha,\omega$-diiodo compounds made by the process described above include $I(CF_2)_3CH_2CF_2I$, $I(CF_2)_4CH_2CF_2I$, $I(CF_2)_5CH_2CF_2I$, $ICF_2CH_2(CF_2)_3CH_2CF_2I$, $ICF_2CH_2(CF_2)_4CH_2CF_2I$, $ICF_2CH_2(CF_2)_5CH_2CF_2I$, and combinations thereof.

In one embodiment, the partially fluorinated $\alpha,\omega$-diiodo compounds of the present disclosure may be used as chain transfer agents in polymer syntheses or, as will be described below, can be used to generate other fluorinated compounds.

In the present disclosure the VDF substituted perfluorinated diiodido-compound from Method I may be further treated with a base or base-like compound in an aprotic organic solution to dehydrofluorinate.

Method II

In Method II, a partially fluorinated $\alpha,\omega$-diiodo compound is dehydroiodinated to form a partially fluorinated iodoalkene compound (i.e., a compound comprising a terminal iodine atom on one side of the molecule and a terminal carbon-carbon double bond on the opposing side of the moelecule). Such partially fluorinated iodoalkene compounds may be used as a cure site monomer.

In Method II, the partially fluorinated $\alpha,\omega$-diiodo compound is the 1:1 adduct from Method I, which then undergoes dehydroiodination to remove HI from the molecule forming a terminal carbon-carbon double bond.

Generally, at least a mole equivalent of the base or base-like compound to the VDF substituted perfluorodiiodide should be used to favor the formation of the partially fluorinated iodo alkene compound.

Base and base-like compounds include those known in the art, for example, methoxides, KOH, NaOH, alkyl amines, LiCl in dimethylformamide, etc.

In one embodiment the reaction may be conducted at a temperature of at least 10, 20, 23, 25, 30, or even 35° C.; at most 70, 80, 90, 100, 150, 200, or even 220° C.

In one embodiment, the reaction is conducted in the presence of a solvent. Typical solvents include, for example, aproticorganic solvents such as butyl nitrile and dimethylformamide.

The resulting partially fluorinated terminal iodo alkene compounds may be isolated and purified by known methods.

In one embodiment, partially fluorinated iodoalkene compounds made by the process of Method II include those of Formula (III): $I(CF_2)_a CH=CF_2$ where a is an integer greater than 2 and no more than 20. In one embodiment, Formula III is $I(CF_2)_a CH=CF_2$ wherein a is an odd integer selected from 3 to 11 (in other words 3, 5, 7, 9, or 11).

Exemplary partially fluorinated iodoalkene compounds include: $I(CF_2)_y CH=CF_2$; where y is an integer greater than 2 and no more than 20, such as $I(CF_2)_3 CH=CF_2$, $I(CF_2)_4 CH=CF_2$, $I(CF_2)_5 CH=CF_2$, $I(CF_2)_6 CH=CF_2$, and combinations thereof.

In one embodiment, the partially fluorinated terminal iodoalkene compounds of the present disclosure may be used as cure site monomers in polymer syntheses.

Method III

In Method III, a partially fluorinated $\alpha,\omega$-diiodo compound is dehydroiodinated to form a partially fluorinated iodoalkene compound (i.e., a compound comprising a terminal iodine atom on one side of the molecule and a terminal carbon-carbon double bond on the opposing side of the moelecule), a partially fluorinated dialkene compounds (i.e., compounds comprising a two terminal carbon-carbon double bond on opposing sides of the molecule) or combinations thereof. The partially fluorinated iodoalkene compounds may be used as a cure site monomer, while the partially fluorinated dialkene compounds may be used as a monomer.

In Method III, the partially fluorinated $\alpha,\omega$-diiodo compound is the 1:2 adduct from Method I, which then undergoes dehydroiodination to remove HI from the molecule forming a terminal carbon-carbon double bond. In Method III, this may happen to one or both ends of the partially fluorinated $\alpha,\omega$-diiodo compound.

The dehydroiodination can occur using a base or base-like compounds and the reaction conditions as described above in Method II.

As shown in the exemplary reaction of Method III above, when doing the dehydroiodination, either one or both ends of the partially fluorinated $\alpha,\omega$-diiodo compound (e.g., Formula II) may be dehydroiodinated resulting in, for example, compounds according to Formula IV and V. Further, the ratio of base and base-like compounds to the α,ω-diiodo partially fluorinated compound can be adjusted to favor a particular product. For example, to favor the formation of Formula IV, the ratio of the α,ω-diiodo partially fluorinated compound to an equivalent of the base and base-like compound is 1:0.8 to 1:1.1. To favor the formation of Formula V, the ratio of the α,ω-diiodo partially fluorinated compound to the equivalent of the base and base-like compound is 1:1.8 to 1:2.5.

The resulting partially fluorinated compounds may be isolated and purified by known methods.

In one embodiment, partially fluorinated iodoalkene compounds made by the process of Method III include those of Formula (IV): $CF_2=CH(CF_2)_aCH_2CF_2I$ where a is an integer greater than 2 and no more than 20 (e.g., 3, 4, 6, 8, etc.). In one embodiment, Formula IV is $ICF_2CH_2(CF_2)_aCH=CF_2$ wherein a is an odd integer selected from 3 to 11 (in other words 3, 5, 7, 9, or 11).

Exemplary partially fluorinated iodoalkene compounds include: $CF_2=CH(CF_2)_xCH_2CF_2I$ wherein x is an odd integer selected from 3 to 11 (in other words 3, 5, 7, 9, or 11). Exemplary partially fluorinated iodoalkene compounds include: $ICF_2CH_2(CF_2)_3CH=CF_2$, $I\ CF_2CH_2(CF_2)_4CH=CF_2$, $I\ CF_2CH_2\ (CF_2)_5CH=CF_2$, $I\ CF_2CH_2(CF_2)_6CH=CF_2$, and combinations thereof.

In another embodiment, partially fluorinated dialkene compounds are made by the process of Method III such as those of Formula (V): $CF_2=CH(CF_2)_aCH=CF_2$ where a is an integer greater than 2 and no more than 20. In one embodiment, Formula V is $CF_2=CH(CF_2)_aCH=CF_2$ wherein a is an odd integer selected from 3 to 11 (in other words 3, 5, 7, 9, or 11).

Exemplary partially fluorinated dialkene compounds include: $CF_2=CH(CF_2)_yCH=CF_2$ wherein y is an integer greater than 2 and no more than 20. Exemplary partially fluorinated dialkene compounds include: $CF_2=CH(CF_2)_3CH=CF_2$, $CF_2=CH\ (CF_2)_4CH=CF_2$, $CF_2=CH\ (CF_2)_5CH=CF_2$, $CF_2=CH\ (CF_2)_6CH=CF_2$, and combinations thereof.

In one embodiment, the partially fluorinated terminal iodoalkene compounds of the present disclosure may be used as cure site monomers in polymer syntheses and the partially fluorinated dialkene compounds of the present disclosure may be used as monomers in polymer syntheses.

Polymer Synthesis

In one embodiment, the compounds as disclosed herein (e.g., those of Formulas I, II, III, IV, and V) can be used either individually or together along with additional fluorinated olefins in a fluoropolymer polymerization.

In preparing fluoropolymers, the compounds of Formulas I, II, III, IV, and/or Formula V may be polymerized with one or more fluorinated olefinic monomer(s) to form a fluoropolymer (in other words, a polymer comprising fluorine atoms along the backbone of the polymer).

A fluorinated olefinic monomer is a monomer having a carbon-carbon double bond and comprising at least one fluorine atom and are those monomers other than those partially fluorinated compounds synthesized herein. In other words, they are monomers different than those falling under Formulas III, IV and V, disclosed herein. The fluorinated olefinic monomer may be perfluorinated (or fully fluorinated) or partially fluorinated (comprising at least one hydrogen atom and one fluorine atom).

Exemplary perfluorinated olefinic monomers include: hexafluoropropene (HFP), tetrafluoroethylene (TFE), trifluorochloroethylene (CTFE), perfluoro(alkylvinyl ether), chlorotrifluoroethylene, perfluoro(methyl vinyl ether) (PMVE), perfluoro(propyl vinyl ether) (PPVE), perfluoro(methoxypropyl vinyl ether), perfluoro(ethoxymethyl vinyl ether), $CF_2=CFOCF_2CF_2CF_2OCF_3$, $CF_2=CFOCF_2OCF_2CF_2CF_3$, $CF_2=CFOCF_2OCF_2CF_3$, $CF_2=CFOCF_2OCF_3$, and combinations thereof.

Exemplary partially fluorinated olefinic monomers include: vinyl fluoride (VF), vinylidene fluoride (VDF), pentafluoropropylene (e.g., 2-hydropentafluropropylene), trifluoroethylene, and combinations thereof.

In addition to the fluorinated olefinic monomer, non-fluorinated olefinic monomers may be added. Exemplary non-fluorinated olefinic monomers include: propylene, ethylene, isobutylene, and combinations thereof. Generally, these additional monomers would be used at less than 25 mole percent of the fluoropolymer, preferably less than 10 mole percent, and even less than 3 mole percent.

The fluoropolymers described herein may be obtained by polymerizing the partially fluorinated compounds of the present disclosure in the presence of fluorinated olefinic monomers and optionally additional monomers. Known polymerization techniques including aqueous emulsion polymerization may be used.

The reactor vessel for use in the aqueous emulsion polymerization process is typically a pressurizable vessel capable of withstanding the internal pressures during the polymerization reaction. Typically, the reaction vessel will include a mechanical agitator, which will produce thorough mixing of the reactor contents and heat exchange system. Any quantity of the fluoromonomer(s) may be charged to the reactor vessel. The monomers may be charged batch-wise or in a continuous or semi-continuous manner. The independent rate at which the monomers are added to the kettle will depend on the consumption rate of the particular monomer with time. Preferably, the rate of addition of monomer will equal the rate of consumption of monomer, that is conversion of monomer into polymer.

In one embodiment, a fluorinated surfactant may be used which corresponds to the general formula:

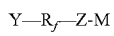

$$Y-R_f-Z-M$$

wherein Y represents hydrogen, Cl or F; $R_f$ represents a linear or branched perfluorinated alkylene having 4 to 10 carbon atoms; Z represents $COO^-$ or $SO_3^-$ and M represents an alkali metal ion or an ammonium ion. Such fluorinated surfactants include fluorinated alkanoic acid and fluorinated alkanoic sulphonic acids and salts thereof, such as ammonium salts of perfluorooctanoic acid and perfluorooctane sulphonic acid. Also contemplated for use in the preparation of the polymers described herein are fluorinated surfactants of the general formula:

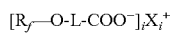

$$[R_f-O-L-COO^-]_iX_i^+$$

wherein L represents a linear partially or fully fluorinated alkylene group or an aliphatic hydrocarbon group, $R_f$ represents a linear partially or fully fluorinated aliphatic group or a linear partially or fully fluorinated group interrupted with one or more oxygen atoms, $X_i^+$ represents a cation having the valence i and i is 1, 2 and 3. Specific examples are described in US 2007/0015937, which is incorporated herein by reference.

Also contemplated for use in the preparation of the polymers described herein are fluorinated polyether surfactants, such as described in U.S. Pat. No. 6,429,258.

In one embodiment, the polymerization is substantially free of an emulsifier. Such emulsifiers may include fluorinated emulsifiers such as fluorinated alkanoic acids and salts thereof; fluorinated alkanoic sulphonic acids and salts thereof; fluoroethoxy alkanoic acids and salts thereof; and combinations thereof. As used here, substantially free of an emulsifier, means less than 0.05%, 0.01%, or even 0.001% by wt of the emulsifier versus the total weight of the dispersion is present, or even no emulsifier is detected in the resulting dispersion.

A chain transfer agent may also be charged to the reaction kettle. Generally, chain transfer agents are added to the polymerization to control the molecular weight of the growing polymer chain. Useful chain transfer agents include $C_2$ to $C_6$ hydrocarbons such as ethane, alcohols, ethers, esters including aliphatic carboxylic acid esters and malonic esters, ketones and halocarbons. Particularly useful chain transfer agents are dialkylethers such as dimethyl ether and methyl tertiary butyl ether. Additions of chain transfer agent in a continuous or semi-continuous way during the polymerization may also be carried out. Exemplary chain transfer agents include: (i) a C1 to C10α,ω-diiodoperfluoroalkane; (ii) $I(CF_2)_zCH_2CH_2I$, wherein z is an even integer from 2 to 10; (iii) $CH_2I_2$; (iv) $I(CF_2)_zCH_2I$, wherein z is an even integer from 2 to 10; and (v) combinations thereof. Exemplary chain transfer agents include 1,3-diiodoperfluoropropane, 1,4-diiodoperfluorobutane, 1,6-diiodoperfluorohexane, and 1,8-diiodoperfluorooctane.

A cure site monomer may also be added to the reaction kettle which are incorporated into the polymer during polymerization and are then used as sites to subsequently crosslink polymer chains. Such cure site monomers may comprise a nitrile-containing group, bromine, and/or iodine. Such cure site monomers are known in the art and can include for example bromodifluoroethylene, bromotrifluoroethylene, iodotrifluoroethylene, 1-bromo-2,2-difluoroethylene, and 4-bromo-3,3,4,4-tetrafluorobutene, $CF_2$=CFO$(CF_2)_5CN$, $CF_2$=CFOCF$_2$CF(CF$_3$)OCF$_2$CF$_2$CN, $CF_2$=CFOCF$_2$CF(CF$_3$)OCF$_2$CF(CF$_3$)CN, $CF_2$=CFOCF$_2$CF$_2$CF$_2$OCF(CF$_3$)CN, $CF_2$=CFOCF$_2$CF(CF$_3$)OCF$_2$CF$_2$CN; and combinations thereof.

When using the cure site monomer of Formula III and/or IV during a polymerization, the chain transfer agent of Formula I and/or II may be used and/or a chain transfer agent selected from (i) a C1 to C10α,ω-diiodoperfluoroalkane; (ii) $I(CF_2)_zCH_2CH_2I$, wherein z is an even integer from 2 to 10; (iii) $CH_2I_2$; (iv) $I(CF_2)_zCH_2I$, wherein z is an even integer from 2 to 10; and (v) combinations thereof.

The polymerization is usually initiated after an initial charge of monomer by adding an initiator or initiator system to the aqueous phase. For example, peroxides can be used as free radical initiators. Specific examples of peroxide initiators include, hydrogen peroxide, diacylperoxides such as diacetylperoxide, dipropionylperoxide, dibutyrylperoxide, dibenzoylperoxide, benzoylacetylperoxide, diglutaric acid peroxide and dilaurylperoxide, and further water soluble per-acids and water soluble salts thereof such as for example ammonium, sodium or potassium salts. Examples of per-acids include peracetic acid. Esters of the peracid can be used as well and examples thereof include tertiary-butylperoxyacetate and tertiary-butylperoxypivalate. A further class of initiators that can be used are water soluble azo-compounds. Suitable redox systems for use as initiators include for example a combination of peroxodisulphate and hydrogen sulphite or disulphite, a combination of thiosulphate and peroxodisulphate or a combination of peroxodisulphate and hydrazine. Further initiators that can be used are ammonium-alkali- or earth alkali salts of persulfates, permanganic or manganic acid or manganic acids. The amount of initiator employed is typically between 0.03 and 2% by weight, preferably between 0.05 and 1% by weight based on the total weight of the polymerization mixture. The full amount of initiator may be added at the start of the polymerization or the initiator can be added to the polymerization in a continuous way during the polymerization until a conversion of 70 to 80%. One can also add part of the initiator at the start and the remainder in one or separate additional portions during the polymerization. Accelerators such as for example water-soluble salts of iron, copper and silver may also be added.

During the initiation of the polymerization reaction, the sealed reactor kettle and its contents are conveniently preheated to the reaction temperature. Polymerization temperatures may be from 20° C., from 30° C., or even from 40° C. and may further be up to 100° C., up to 110° C., or even up to 150° C. The polymerization pressure may range, for instance, from 4 to 30 bar, in particular from 8 to 20 bar. The aqueous emulsion polymerization system may further comprise auxiliaries, such as buffers and complex-formers.

The amount of polymer solids that can be obtained at the end of the polymerization is typically at least 10% by weight, or even at least 20% by weight, and up to 40% by weight, and even up to 45% by weight; and the average particle size of the resulting fluoropolymer is typically between 50 nm and 500 nm.

After polymerization, the polymer dispersion may be coagulated and washed as is known in the art to form a polymer gum.

In one embodiment the polymer of the present disclosure comprises at least 0.05, 0.1, 0.2 or even 0.4% by weight iodine relative to the total weight of the polymer gum. In one embodiment the polymer gum of the present disclosure comprises at most 0.5, 0.75, 1, or even 1.5% by weight iodine relative to the total weight of the polymer gum.

The polymer gums of the present disclosure are partially fluorinated polymers. As disclosed herein a partially fluorinated polymer comprises at least one hydrogen and at least one fluorine atom on the backbone of the polymer.

Exemplary fluoropolymers include: a TFE/propylene copolymer, a TFE/propylene/VDF copolymer, a VDF/HFP copolymer, a TFE/VDF/HFP copolymer, a TFE/PMVE copolymer, a TFE/CF$_2$=CFOCF$_3$F$_7$ copolymer, a TFE/CF$_2$=CFOCF$_3$/CF$_2$=CFOC$_3$F$_7$ copolymer, a TFE/CF$_2$=C(OC$_2$F$_5$)$_2$ copolymer, a TFE/ethyl vinyl ether (EVE) copolymer, a TFE/butyl vinyl ether (BVE) copolymer, a TFE/EVE/BVE copolymer, a VDF/CF$_2$=CFOC$_3$F$_7$ copolymer, an ethylene/HFP copolymer, a TFE/HFP copolymer, a CTFE/VDF copolymer, a TFE/VDF copolymer, a TFE/VDF/PMVE/ethylene copolymer, and a TFE/VDF/CF$_2$=CFO(CF$_2$)$_3$OCF$_3$ copolymer.

Curing

In one embodiment of the present disclosure, the fluoropolymer of the present disclosure may be cured with peroxide curing agents including organic peroxides. In many cases it is preferred to use a tertiary butyl peroxide having a tertiary carbon atom attached to a peroxy oxygen.

Exemplary peroxides include: 2,5-dimethyl-2,5-di(t-butylperoxy)hexane; dicumyl peroxide; di(2-t-butylperoxyisopropyl)benzene; dialkyl peroxide; bis(dialkyl peroxide); 2,5-dimethyl-2,5-di(tertiarybutylperoxy)3-hexyne; dibenzoyl peroxide; 2,4-dichlorobenzoyl peroxide; tertiarybutyl perbenzoate; α,α'-bis(t-butylperoxy-diisopropylbenzene); t-butyl peroxy isopropylcarbonate, t-butyl peroxy 2-ethylhexyl carbonate, t-amyl peroxy 2-ethylhexyl carbonate, t-hexylperoxy isopropyl carbonate, di[1,3-dimethyl-3-(t-butylperoxy)butyl] carbonate, carbonoperoxoic acid, O,O'-1,3-propanediyl OO,O'O'-bis(1,1-dimethylethyl) ester, and combinations thereof.

The amount of peroxide curing agent used generally will be at least 0.1, 0.2, 0.4, 0.6, 0.8, 1, 1.2, or even 1.5; at most 2, 2.25, 2.5, 2.75, 3, 3.5, 4, 4.5, 5, or even 5.5 parts by weight per 100 parts of fluoropolymer.

In peroxide cure systems, it is often desirable to include a coagent. Those skilled in the art are capable of selecting conventional coagents based on desired physical properties. Exemplary coagents include: tri(methyl)allyl isocyanurate (TMAIC), triallyl isocyanurate (TAIC), tri(methyl)allyl cyanurate, poly-triallyl isocyanurate (poly-TAIC), triallyl cyanurate (TAC), xylylene-bis(diallyl isocyanurate) (XBD), N,N'-m-phenylene bismaleimide, diallyl phthalate, tris(diallylamine)-s-triazine, triallyl phosphite, 1,2-polybutadiene, ethyleneglycol diacrylate, diethyleneglycol diacrylate, and combinations thereof. Another useful coagent may be represented by the formula $CH_2=CH-R_f-CH=CH_2$ wherein $R_f$ may be a perfluoroalkylene of 1 to 8 carbon atoms. Such coagents provide enhanced mechanical strength to the final cured elastomer. They generally are used in amount of at least 0.5, 1, 1.5, 2, 2.5, 3, 4, 4.5, 5, 5.5, or even 6; at most 4, 4.5, 5, 5.5, 6, 7, 8, 9, 10, 10.5, or even 11 parts by weight per 100 parts of the fluoropolymer.

The fluoropolymer compositions can also contain a wide variety of additives of the type normally used in the preparation of elastomeric compositions, such as pigments, fillers (such as carbon black), pore-forming agents, and those known in the art.

Metal oxides are traditionally used in peroxide curing. Exemplary metal oxides include: $Ca(OH)_2$, CaO, MgO, ZnO, and PbO. In one embodiment, the curable fluoropolymer is essentially free of metal oxide (i.e., the composition comprises less than 1, 0.5, 0.25, 0.1, or even less than 0.05 parts per 100 parts of the fluoroelastomer). In one embodiment, the curable fluoropolymer comprises metal oxide. For example, at least 1.5, 2, 4, 5, or even 6 parts metal oxide per 100 parts of the fluoropolymer.

In the present curing process, the fluoropolymer gum, along with the required amounts of peroxide, coagent, and other components, is compounded by conventional means, such as in a two-roll mill, at elevated temperatures. The fluoropolymer gum is then processed and shaped (for example, in the shape of a hose or hose lining) or molded (for example, in the form of an O-ring). The shaped article can then be heated to cure the gum composition and form a cured elastomeric article.

The cured fluoropolymers are particularly useful as seals, gaskets, and molded parts in systems that are exposed to elevated temperatures and/or corrosive materials, such as in automotive, chemical processing, semiconductor, aerospace, and petroleum industry applications, among others. Because the fluoropolymers may be used in sealing applications, it is important that the polymers perform well under compression. Compressive sealing is based on the ability of an elastomer to be easily compressed and develop a resultant force that pushes back on the mating surfaces. The ability of a material to maintain this resultant force as a function of time over a range of environmental conditions is important to long term stability. As a result of thermal expansion, stress relaxation, and thermal aging, the initial sealing forces will decay over time. By determining the retained sealing force, elastomeric materials can be evaluated for their sealing force retention under a range of conditions, particularly under high temperature conditions, such as 200° C., 225° C., 250° C., and even 275° C.

Exemplary embodiments of the disclosure include:

Embodiment 1: A composition comprising a partially fluorinated compound selected from the group consisting of:
(a) $I(CF_2)_xCH_2CF_2I$;
(b) $ICF_2CH_2(CF_2)_xCH_2CF_2I$;
(c) $I(CF_2)_yCH=CF_2$;
(d) $CF_2=CH(CF_2)_yCH_2CF_2I$; and
(e) $CF_2=CH(CF_2)_yCH=CF_2$
wherein x is an odd integer selected from 3 to 11, and y is an integer greater than 2.

Embodiment 2. A polymer composition comprising the polymerized reaction product of the following reactants:
(a) a first compound selected from the partially fluorinated compound of embodiment 1; and
(b) a second compound comprising a fluorinated olefinic monomer.

Embodiment 3. The polymer composition of embodiment 2, wherein the a second compound is selected from: hexafluoropropylene, trifluoroethylene, fluoroethylene, vinylidene fluoride, tetrafluoroethylene, perfluoro(methyl vinyl ether), perfluoro(propyl vinyl ether), perfluoro(methoxypropyl vinyl ether), perfluoro(ethoxymethyl vinyl ether), chlorotrifluoroethylene, and combinations thereof.

Embodiment 4. The polymer composition of any one of embodiments 2 or 3, wherein the reactants further include (c) a chain transfer agent, wherein the chain transfer agent is selected from the group consisting of: a C1 to C10α,ω-diiodoperfluoroalkane; $I(CF_2)_zCH_2CH_2I$, wherein z is an integer greater than 2; $CH_2I_2$; $I(CF_2)_zCH_2CF_2I$ wherein z is an integer greater than 2; and combinations thereof.

Embodiment 5. The polymer composition of embodiment 4, wherein the chain transfer agent is 1,3-diiodoperfluoropropane or 1,4-diiodoperfluorobutane.

Embodiment 6. The polymer composition of any one of embodiments 2 to 5, wherein at least one of x or y is 3.

Embodiment 7. The polymer composition of any one of embodiments 2 to 6, wherein the reactants further include (d) a non-fluorinated olefinic monomer.

Embodiment 8. The polymer composition of any one of embodiments 2 to 7, wherein the polymer composition comprises 0.05 to 1% by weight of iodine.

Embodiment 9. An article comprising the cured polymer composition according to any one of embodiments 2 to 8.

Embodiment 10. A method of making a polymer comprising:
(c) providing a first fluorinated olefinic monomer comprising the partially fluorinated compound, $I(CF_2)_yCH=CF_2$ wherein y is an integer greater than 2 of embodiment 1; a second fluorinated olefinic monomer; and an initiator; and
(d) polymerizing the first and second fluorinated olefinic monomers in the presence of the initiator to form a polymer.

Embodiment 11. A method of making a polymer comprising:
(a) providing a first fluorinated olefinic monomer comprising the partially fluorinated compound, $CF_2=CH(CF_2)_yCH=CF_2$ wherein y is an integer greater than 2 of embodiment 1; a second fluorinated olefinic monomer; and an initiator; and
(b) polymerizing the first and second fluorinated olefinic monomers in the presence of the initiator to form a polymer.

Embodiment 12. The method of any one of embodiments 10-11, further comprising polymerizing in the presence of a chain transfer agent.

Embodiment 13. The method of embodiment 12, wherein the chain transfer agent is 1,3-diiodoperfluoropropane or 1,4-diiodoperfluorobutane.

Embodiment 14. The method of any one of embodiments 10-13, wherein the second fluorinated olefinic monomer is selected from: hexafluoropropylene, trifluoroethylene, fluoroethylene, vinylidene fluoride, tetrafluoro ethylene, perfluoro (methyl vinyl ether), perfluoro (propyl vinyl ether), perfluoro(methoxypropyl vinyl ether), perfluoro(ethoxymethyl vinyl ether), chlorotrifluoroethylene, and combinations thereof.

Embodiment 15. The method of any one of embodiments 10-14, wherein the first and second fluorinated olefinic monomers are polymerized in an emulsion polymerization.

Embodiment 16. The method of any one of embodiments 10-15, wherein the polymerizing step is substantially free of an emulsifier wherein the emulsifier is selected from fluorinated alkanoic acids and salts thereof; fluorinated alkanoic sulphonic acids and salts thereof; fluoroethoxy alkanoic acids and salts thereof; and combinations thereof.

Embodiment 17. A method of making a partially fluorinated compound comprising reacting a molecule of the formula $I(CF_2)_xI$ with 1,1-difluoroethylene to form $I(CF_2)_xCH_2CF_2I$, wherein x is an odd integer selected from 3 to 11.

Embodiment 18. The method of embodiment 17, further comprising dehydroiodinating $I(CF_2)_xCH_2CF_2I$ to form an partially fluorinated iodo alkene compound of the formula $I(CF_2)_xCH=CF_2$ wherein x is an odd integer selected from 3 to 11.

Embodiment 19. A method of making a partially fluorinated compound comprising reacting a molecule of the formula $I(CF_2)_xI$ with 1,1-difluoroethylene to form $ICF_2—CH_2(CF_2)_yCH_2CF_2I$, wherein y is an integer greater than 2.

Embodiment 20. The method of embodiment 19, further comprising dehydroiodinating $ICF_2—CH_2(CF_2)_yCH_2CF_2I$, to form (i) a partially fluorinated diene compound of the formula $CF_2=CH(CF_2)_yCH_2CF_2I$; (ii) a partially fluorinated diene compound of the formula $CF_2=CH(CF_2)_yCH=CF_2$; and (iii) combinations thereof, wherein y is an integer greater than 2.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: g=gram, min=minute, mol=mole, hr=hour, mL=milliliter; wt=weight.

Materials

| Material Name | Description |
|---|---|
| Iodine | Available from Alpha Aesar, A Johnson Matthey Company, Ward Hill, MA |
| Nickel catalyst | Available under the trade designation "PRO-PAK DISTILLATION PACKING (0.24")" from Cannon Instrument Company, State College, Pennsylvania. This is a nickel ribbon with over 1000 tiny holes per in$^2$ (over 155 tiny holes per cm$^2$). |
| HFPO | Hexafluoropropylene oxide, available from E.I. DuPont de Nemours and Company, Wilmington, DE |
| Perfluorobutane disulfonyl fluoride | $FSO_2C_4F_8SO_2F$ can be made as described in U.S. Pat. No. 2,732,398. |
| Sodium borohydride | Available from Sigma-Aldrich Chemical Company |
| Sodium persulfate | Available from Sigma-Aldrich Chemical Company |
| t-Butyl-2-ethyl hexanoate peroxide | Available from United Initiators, Inc., Elyria, OH |
| 1,4-Diiodooctafluorobutane | $I(CF_2)_4I$, available from FSUE Russian Scientific Center of Applied Chemistry Perm Branch, Russia. |
| N990 carbon black | Available under the trade designation "THERMAX FLOFORM MEDIUM THERMAL CARBON BLACK N990", ASTM N990 from Cancarb Ltd., Medicine Hat, Alberta, Canada |
| 2,5-Dimethyl-2,5-di(t-butylperoxy)-hexane | 50% active, available under the trade designation "VAROX DBPH-50" from R. T. Vanderbilt, Norwalk, CT |
| TAIC | Triallylisocyanurate (98%) available under the trade designation "TAIC" from Nippon Kasei, Japan |
| HFE-7500 | 3-ethoxy-dodecafluoro-2-trifluoromethyl-hexane, available under the trade designation "3M NOVEC ENGINEERED FLUID HFE-7500" from 3M Co., St. Paul, MN, USA. |

$^1H/^{19}F$-NMR Characterization

The 1D and 2D FT-NMR spectra were acquired and used for compositional analysis using a Varian VNMRS 400 FT-NMR spectrometer (Varian Inc., Palo Alto, Calif.) that was operating with a 5 mm inverse-detection gradient probe at a temperature of about 22-23° C.

Cure Rheology

Cure rheology tests were carried out using uncured, compounded samples using a rheometer (Alpha Technology RPA 2000 in Moving Die Rheometer (MDR) mode by Alpha Technology, A Dynisco Company, Akron, Ohio) in accordance with ASTM D 5289-95 at 177° C., no pre-heat, 12 minute elapsed time, and a 0.5 degree arc. Both the minimum torque (ML) and highest torque attained during a specified period of time when no plateau or maximum torque (MH) was obtained were measured. Also measured were the time for the torque to increase 2 units above ML (ts2); the time for the torque to reach a value equal to ML+0.5 (MH–ML), (t'50); and the time for the torque to reach ML+0.9 (MH–ML), (t'90) as well as the tan delta (δ) at MH and ML. Results are reported in Table 1.

Physical Properties

Mooney viscosity or compound Mooney viscosity was determined in accordance with ASTM D1646-06 TYPE A by a MV 2000 instrument (available from Alpha Technologies, Ohio, USA) using large rotor (ML 1+10) at 121° C. Results are reported in Mooney units.

Example 1

Preparation of 1,3-Diiodohexafluoropropane from HFPO

A 300 mL Hastelloy B-2 autoclave (commercially available from the Superpressure Division of Newport Scientific Inc., Jessup, Md.) was charged with 24.5 g of iodine and 2.5 g of nickel catalyst. The autoclave was charged with nitrogen and evacuated three times. The autoclave was cooled down with dry ice and charged with 58 g of HFPO. The autoclave was placed in a rocker where it was heated to 170° C. for 12 hrs. The autoclave was allowed to cool to room temperature before the gases produced were vented and 36 g of a dark liquid was obtained. The crude mixture was analyzed by $^{19}F$ and $^{1}H$ NMR (nuclear magnetic resonance) with the following results: I—$CF_2$—I (0.0036 absolute wt %), I—$(CF_2)_2$—I (<0.00005%), I—$(CF_2)_3$—I (92.2%), I—$(CF_2)_4$—I (0.41%), I—$(CF_2)_5$—I (5.4%), I—$(CF_2)_8$—I (0.27%) plus small amounts of various other monoiodo and diiodo compounds, partially fluorinated compounds, acid fluorides, carboxylic acids, alkenes, etc.

Example 2

Preparation of 1,4-Diiodooctafluorobutane from $FSO_2C_4F_8SO_2F$

Perfluorobutane disulfonyl fluoride, $FSO_2C_4F_8SO_2F$, 186 g (0.5 mol) was reduced in a 3-liter 3-neck round bottom flask equipped with a mechanical stirrer, condenser, addition funnel and a thermocouple by addition to 76 g (2.0 mol) sodium borohydride in 600 g 2-propanol. The addition rate was done over three hours keeping the reaction temperature below 40° C. After addition, the reaction was heated to 75° C. for one hour. The reaction was cooled to 25° C. and 298 g of 33% sulfuric acid was added followed by filtration to get a $HOSOC_4F_8SO_2H$ solution. A 3-liter 3-neck round bottom flask was charged with iodine, 300 g (1.19 mol), sodium persulfate, 282 g (1.19 mol), 500 g distilled water and 500 g 2-propanol stirred and heated to 55° C. The $HOSOC_4F_8SO_2H$ solution was added over one hour. After addition, the reaction was heated to 75° C. and held for one hour. Distillation of product and solvent were collected in a receiver by heating the pot mixture up to 108° C. The product and solvent mixture was treated with sodium sulfite, (70 g of a 10% aqueous solution) to get to a light yellow solution. Additional water was added to get the fluorochemical to form a lower phase and the fluorochemical product was washed twice with 100 g of distilled water. Vacuum distillation gave 1,4-diiodooctafluorobutane, I, 147 g (0.33 mol) having a boiling point of 85° C./100 torr for a 66% yield confirmed by F and HNMR.

Example 3

Preparation of $CF_2$=CH—$C_3F_6$—I

A 600 ml Parr™ reactor was evacuated and charged with 1,3-diiodohexafluoropropane, I—$C_3F_6$—I, 250 g (0.62 mol) (made from Example 1) and t-butyl-2-ethyl hexanoate peroxide, 12 g (0.06 mol) and stirred. The reactor was heated to 75° C. and 1,1-difluoroethylene, 30 g (0.47 mol) was added at 40 psi (pounds per square inch) over four hours and reacted for 20 hrs. The reactor was cooled to 25° C. and 269 g of product mixture was drained from the reactor. Vacuum distillation gave $ICF_2CH_2C_3F_6I$, 126 g (0.27 mol) boiling at 125° C./90 torr vacuum. A higher boiling cut contained mainly $ICF_2CH_2C_3F_6CH_2CF_2I$, 46 g (0.09 mol). A charge of tributylamine, 95 g (0.51 mol), reacted with 126 g (0.27 mol) $ICF_2CH_2C_3F_6I$ added over two hours. The reaction temperature reached 45° C. and after cooling to 25° C., 250 g of 20% $H_2SO_4$ was added. Vacuum distillation at 90° C./90 torr vacuum distilled out water and a mixture containing approximately 91% of $CF_2$=CH$(CF_2)_3$I, 4.1% of $CF_2$=CH$(CF_2)_3$CH=$CF_2$, 1.0% of $CF_3CH_2(CF_2)_3$I, 1.0% of $CF_2$=CH$(CF_2)_3CH_2CF_2$H and 0.3% of I$(CF_2)_3$I. 1-iodo 1,1,2,2,3,3,5,5-octafluoropentene, $IC_3F_6CH$=$CF_2$, 64 g (0.19 mol) having a boiling point of 94° C. was isolated in a 40% yield based on 1,1-difluoroethylene. 19FNMR chemical shifts (−) ppm upfield of internal $CFCl_3$, ICF2(a)CF2(b)CF2(c)CH=CF2(d,e), a: −58.1, t/t; b: −115.5, m; c: −106.9, m; d: −71.2, d/t; e: −72.7, d/t; 1HNMR (+) ppm downfield of internal TMS, —CH(f)=CF2, f: 4.67, d/t.

Example 4

Preparation of $CF_2$=CH—$C_4F_8$—I

A 600 ml Parr™ reactor was evacuated and charged with 1,4-diiodooctafluorobutane, I—$C_4F_8$—I, 398 g (0.88 mol) (made from Example 2) and t-butyl-2-ethyl hexanoate peroxide, 38 g (0.18 mol) and stirred. The reactor was heated to 72° C. and 1,1-difluoroethylene, 30 g (0.47 mol) was added at 40 psi over six hours and reacted for 20 hrs. The reactor was cooled to 25° C. and 439 g of product mixture was drained from the reactor. Vacuum distillation gave $ICF_2CH_2C_4F_8I$, 159 g (0.23 mol) boiling at 105° C./17 torr vacuum. Additional vacuum distillation gave $ICF_2CH_2C_4F_8CH_2CF_2I$, 87 g (0.16 mol) boiling at 150° C./17 torr vacuum. A charge of tributylamine, 83 g (0.44 mol) was reacted with 117 g (0.23 mol) of $ICF_2CH_2C_4F_8I$ added over two hours. The reaction temperature reached 38° C. and after cooling to 25° C. 250 g of 20% $H_2SO_4$ was added. Vacuum distillation at 90° C./90 torr vacuum distilled out water and a mixture containing approximately 94.1% of $CF_2$=CH$(CF_2)_4$I, 1.7% of $CF_2$=CH$(CF_2)_4$CH=$CF_2$, 0.8% of $CF_3CH_2(CF_2)_4$I, 0.6% of $CF_3CH$=$(CF_2)_3$I and 0.4% of I$(CF_2)_4$I. 1-iodo-1,1,2,2,3,3,4,4,6,6-decafluorohexene, $IC_4F_8CH$=$CF_2$, 56 g (0.14 mol) having a boiling point of 126° C. was isolated in a 30% yield based on 1,1-difluoroethylene. 19FNMR chemical shifts (−) ppm upfield of internal $CFCl_3$, ICF2(a)CF2(b)CF2(c)CF2(d)CH=CF2(e,f), a: −58.8, t/t; b: −113.0, m; c: −123.3; d: −108.6; e: −71.0, d/m; f: −72.2, d/m; 1HNMR (+) ppm downfield of internal TMS, —CH(g)=CF2, g: 5.85, d/q.

Example 5

Preparation of $CF_2$=CH—$C_4F_8$—I

A 600 ml Parr™ reactor was evacuated and charged with 1,4-diiodooctafluorobutane, I—$C_4F_8$—I, 375 g (0.83 mol) (made from Example 2) and stirred. The reactor was heated to 206° C. and 1,1-difluoroethylene, 52 g (0.81 mol) was added at 98 psi over 11 hours and reacted for one hour. The reactor was cooled to 25° C. and 410 g of product mixture was drained from the reactor. Vacuum distillation gave $ICF_2CH_2C_4F_8I$, 152 g (0.29 mol) boiling at 105° C./17 torr vacuum. A charge of tributylamine, 98 g (0.52 mol) was reacted with 145 g (0.28 mol) of $ICF_2CH_2C_4F_8I$ added over one hour. The reaction temperature reached 53° C. and after cooling to 25° C., 150 g of 33% $H_2SO_4$ was added. The mixture was stirred and phase split. To the bottom product phase was added 100 g distilled water. Vacuum distillation at 90° C./90 torr vacuum distilled out water and 1-iodo-1,1,2,2,3,3,4,4,6,6-decafluorohexene, $IC_4F_8CH$=$CF_2$, 76 g (0.19 mol) for a 24% yield based on 1,1-difluoroethylene.

Example 6

Preparation of $CF_2$=CH—$C_4F_8$—CH=$CF_2$

A charge of tributylamine, 83 g (0.44 mol) was reacted with 87 g (0.16 mol) of $ICF_2CH_2C_4F_8CH_2CF_2I$ (made from Example 4) added over one hour. The reaction temperature reached 48° C. and after cooling to 25° C., 250 g of 20% $H_2SO_4$ was added. Vacuum distillation at 90° C./90 torr vacuum distilled out water and a mixture containing approximately 60.9% of $CF_2$=$CH(CF_2)_4CH$=$CF_2$, 20.2% of $CF_2$=$CH(CF_2)_4I$, 8.2% $CF_3CF_2(CF_2)_4I$ and 0.05% of $I(CF_2)_4I$. 1,1,3,3,4,4,5,5,6,6,8,8-dodecafluorooctodiene, $CF_2$=$CH$—$C_4F_8CH$=$CF_2$, 25 g (0.08 mol) having a boiling point of 92° C. was isolated. 19FNMR chemical shifts (−) ppm upfield of internal CFCl3, CF2(a,b)=CHCF2(c)CF2(d)CF2(d)CF2(c)CH=CF2(a,b), a: −71.4, d/m; b: −72.6, d/m; c: −108.6, m; d: −124.0, m; 1HNMR (+) ppm downfield of internal TMS, —CH(g)=CF2, g: 4.64, d/t.

Example 7

Preparation of Fluoroelastomer

A 4 liter reactor was charged with 2,250 grams of water, 2 grams of ammonium persulfate (APS, (NH4)2S2O8), and 8 grams of 50% aqueous solution of potassium phosphate dibasic (K2HPO4), 3.5 grams of HFE-7500, and 3.5 grams of the isolated product made in Example 3 above, comprising a mixture containing approximately 91% of $CF_2$=$CH(CF_2)_3I$, 4.1% of $CF_2$=$CH(CF_2)_3CH$=$CF_2$, 1.0% of $CF_3CH_2(CF_2)_3I$, 1.0% of $CF_2$=$CH(CF_2)_3CH_2CF_2H$ and 0.3% of $I(CF_2)_3I$. The reactor was evacuated, the vacuum was broken and it was pressurized with nitrogen to 25 psi (0.17 MPa). This vacuum and pressurization was repeated three times. After removing oxygen, the reactor was heated to 80° C. and the vacuum was broken and pressurized to 40 psi (0.28 MPa) with hexafluoropropylene (HFP). The reactor was then charged with tetrafluoroethylene (TFE), vinylidene fluoride (VDF) and the above described hexafluoropropylene (HFP), bringing reactor pressure to 200 psi (1.38 MPa). Total precharge of TFE, VDF and HFP was 25.8 grams, 78.9 grams and 243.6 grams, respectively. The reactor was agitated at 650 rpm. As reactor pressure dropped due to monomer consumption in the polymerization reaction, TFE, VDF and HFP were continuously fed to the reactor to maintain the pressure at 200 psi (1.38 MPa). The ratios of HFP/VDF and TFE/VDF were 0.61 and 0.23 by weight, respectively. After 4.5 hours the monomer feed was discontinued and the reactor was cooled. The resulting dispersion had a solid content of 31.2 wt. % and a pH of 3.3. The dispersion particle size was 240 nm and total amount of dispersion was 3,873 grams.

For the coagulation, 942 g of the dispersion made as described above was added to 2,320 mL of a 1.25 wt % $MgCl_2$ in water solution. The crumb was recovered by filtering the coagulate through cheese cloth and gently squeezing to remove excess water. The crumb was returned to the coagulation vessel and rinsed with deionized water a total of 3 times. After the final rinse and filtration, the crumb was dried in a 130° C. oven for 16 hours. The resulting fluoroelastomer raw gum had a Mooney viscosity of 53 at 121° C. The fluoroelastomer by FT-IR analysis contained 16.0 wt % copolymerized units of TFE, 48.9 wt % copolymerized units of VDF and 33.2 wt % copolymerized units of HFP. The fluorine content was 67.8 wt %.

A fluoroelastomer compound was prepared using a 6" two roll mill by compounding 100 parts of the fluoroelastomer raw gum from above with 30 parts of N990 carbon black, 2 parts of 2,5-dimethyl-2,5-di(t-butylperoxy)-hexane, and 3 parts of TAIC.

The cure rheology of the samples was investigated by testing uncured, compounded mixtures using the Alpha Technology RPA 2000 with MDR (Moving Die Rheometer) mode and the procedure described in ASTM D 5289-95. The fluoroelastomer compound exhibited good curing properties and the 90% cure time (t'90) was 0.1.6 minutes and delta torque (MH-ML) was 8.1 lb-in (9.2 dNm). The test results are summarized in Table 1.

TABLE 1

| Cure rheology (MDR) 12 min @177° C. | Example 7 |
| --- | --- |
| ML (in-lb) | 0.8 |
| MH (in-lb) | 8.9 |
| Δ torque (in-lb) | 8.1 |
| ts2 (min) | 0.6 |
| t'50 (min) | 0.8 |
| t'90 (min) | 1.6 |
| tan δ ML | 1.4 |
| tan δ MH | 0.259 |

Foreseeable modifications and alterations of this invention will be apparent to those skilled in the art without departing from the scope and spirit of this invention. This invention should not be restricted to the embodiments that are set forth in this application for illustrative purposes. To the extent that there is a conflict or discrepancy between this specification and the disclosure in any document incorporated by reference herein, this specification will control.

What is claimed is:

1. A composition comprising a partially fluorinated compound selected from the group consisting of:
    (a) $I(CF_2)_xCH_2CF_2I$;
    (b) $ICF_2CH_2(CF_2)_xCH_2CF_2I$;
    (c) $I(CF_2)_yCH$=$CF_2$;
    (d) $CF_2$=$CH(CF_2)_yCH_2CF_2I$; and
    (e) $CF_2$=$CH(CF_2)_yCH$=$CF_2$
    wherein x is an odd integer selected from 3 to 11, and y is an odd integer selected from 3 to 11.

2. A polymer composition comprising the polymerized reaction product of the following reactants:
    (a) a first compound selected from the partially fluorinated compound of claim 1; and
    (b) a second compound comprising a fluorinated olefinic monomer.

3. The polymer composition of claim 2, wherein the a second compound is selected from: hexafluoropropylene, trifluoroethylene, fluoroethylene, vinylidene fluoride, tetrafluoroethylene, perfluoro(methyl vinyl ether), perfluoro(propyl vinyl ether), perfluoro(methoxypropyl vinyl ether), perfluoro(ethoxymethyl vinyl ether), chlorotrifluoroethylene, and combinations thereof.

4. The polymer composition of claim 2, wherein the reactants further include (c) a chain transfer agent, wherein the chain transfer agent is selected from the group consisting of: a C1 to C10 α,ω-diiodoperfluoroalkane; $I(CF_2)zCH_2CH_2I$, wherein z is an integer greater than 2; $CH_2I_2$; $I(CF_2)_zCH_2CF_2I$ wherein z is an integer greater than 2; and combinations thereof.

5. The polymer composition of claim 2 wherein at least one of x or y is 3.

6. An article comprising the cured polymer composition according to claim 2.

7. A method of making a polymer comprising:
    (a) providing a first fluorinated olefinic monomer comprising the partially fluorinated compound selected from at least one of $I(CF_2)_yCH$=$CF_2$ and $CF_2$=$CH(CF_2)_yCH$=$CF_2$ wherein y is an integer greater than 2 of claim 1; a second fluorinated olefinic monomer; and an initiator; and (b) polymerizing the first and second fluorinated olefinic monomers in the presence of the initiator to form a polymer.

8. The polymer composition of claim 4, wherein the chain transfer agent is 1,3-diiodoperfluoropropane or 1,4-diiodoperfluorobutane.

9. The polymer composition of claim 2, wherein the reactants further include (d) a non-fluorinated olefinic monomer.

10. The polymer composition of claim 2, wherein the polymer composition comprises 0.05 to 1% by weight of iodine.

11. The method of claim 7, further comprising polymerizing in the presence of a chain transfer agent.

12. The method of claim 11, wherein the chain transfer agent is 1,3-diiodoperfluoropropane or 1,4-diiodoperfluorobutane.

13. The method of claim 7, wherein the second fluorinated olefinic monomer is selected from: hexafluoropropylene, trifluoroethylene, fluoroethylene, vinylidene fluoride, tetrafluoroethylene, perfluoro(methyl vinyl ether), perfluoro(propyl vinyl ether), perfluoro(methoxypropyl vinyl ether), perfluoro(ethoxymethyl vinyl ether), chlorotrifluoroethylene, and combinations thereof.

14. The method of claim 7, wherein the first and second fluorinated olefinic monomers are polymerized in an emulsion polymerization.

15. The method of claim 7, wherein the polymerizing step is substantially free of an emulsifier wherein the emulsifier is selected from fluorinated alkanoic acids and salts thereof; fluorinated alkanoic sulphonic acids and salts thereof; fluoroethoxy alkanoic acids and salts thereof; and combinations thereof.

* * * * *

UNITED STATES PATENT AND TRADEMARK OFFICE
CERTIFICATE OF CORRECTION

PATENT NO. : 9,452,960 B2  
APPLICATION NO. : 14/649666  
DATED : September 27, 2016  
INVENTOR(S) : Guerra et al.

Page 1 of 2

It is certified that error appears in the above-identified patent and that said Letters Patent is hereby corrected as shown below:

On the Title Page

Item (56)

Column 2,  
Under "Other Publications," Line 1, delete "telomers" and insert -- telomeres --, therefor.  
Under "Other Publications," Line 3, delete "dliodoperfluoroalkanes"," and insert -- diiodoperfluoroalkanes", --, therefor.

In the Specification

Column 1,  
Line 32, delete "I(CF$_2$)$_x$(CH$_2$CF$_2$I;" and insert -- I(CF$_2$)$_x$CH$_2$CF$_2$I; --, therefor.

Column 5,  
Line 51, delete "I(CF$_2$)—CH$_2$CF$_2$I;" and insert -- I(CF$_2$)$_x$CH$_2$CF$_2$I; --, therefor.

Column 9,  
Line 20, delete "C10α," and insert -- C10 α, --, therefor.  
Line 43, delete "C10α," and insert -- C10 α, --, therefor.

Column 12,  
Line 28, delete "C10α," and insert -- C10 α, --, therefor.

Column 13,  
Lines 7 and 8, delete "perfluoro (methyl" and insert -- perfluoro(methyl --, therefor.  
Line 8, delete "perfluoro (propyl" and insert -- perfluoro(propyl --, therefor.

Signed and Sealed this  
Fourteenth Day of February, 2017

Michelle K. Lee  
*Director of the United States Patent and Trademark Office*

CERTIFICATE OF CORRECTION (continued)
U.S. Pat. No. 9,452,960 B2

Column 15,
Line 43, delete "I," and insert -- I-$C_4F_8$-I, --, therefor.

Column 16,
Line 22, delete "$ICF_2CH_2C_4F_8$1," and insert -- $ICF_2CH_2C_4F_8I$, --, therefor.
Line 51, delete "$ICF_2CH_2C_4F_8$1," and insert -- $ICF_2CH_2C_4F_8I$, --, therefor.

In the Claims

Column 18,
Line 33, in Claim 1, delete "$CF_2$=" and insert -- $CF_2$= --, therefor.
Line 34, in Claim 1, delete "$CF_2$=" and insert -- $CF_2$= --, therefor.
Lines 53 and 54, in Claim 4, delete "$I(CF_2)z$" and insert -- $I(CF_2)_Z$ --, therefor.